United States Patent
Prater et al.

(10) Patent No.: US 8,322,220 B2
(45) Date of Patent: Dec. 4, 2012

(54) NON-DESTRUCTIVE WAFER-SCALE SUB-SURFACE ULTRASONIC MICROSCOPY EMPLOYING NEAR FIELD AFM DETECTION

(75) Inventors: Craig Prater, Goleta, CA (US); Chanmin Su, Ventura, CA (US)

(73) Assignee: Veeco Instruments Inc., Plainview, NY (US)

( * ) Notice: Subject to any disclaimer, the term of this patent is extended or adjusted under 35 U.S.C. 154(b) by 1143 days.

(21) Appl. No.: 12/119,382

(22) Filed: May 12, 2008

(65) Prior Publication Data

US 2008/0276695 A1 Nov. 13, 2008

Related U.S. Application Data

(60) Provisional application No. 60/917,301, filed on May 10, 2007.

(51) Int. Cl.
*G01N 29/06* (2006.01)

(52) U.S. Cl. .............. 73/606; 73/105; 850/5; 850/7; 850/62; 850/63

(58) Field of Classification Search .......... 73/105, 73/606; 850/5, 7, 62, 63
See application file for complete search history.

(56) References Cited

U.S. PATENT DOCUMENTS

| | | | |
|---|---|---|---|
| 4,866,986 A | 9/1989 | Cichanski | |
| 5,675,075 A * | 10/1997 | Arnold et al. | 73/105 |
| 5,852,233 A * | 12/1998 | Arnold et al. | 73/105 |
| 6,389,885 B1 * | 5/2002 | Arnold et al. | 73/105 |
| 6,668,628 B2 | 12/2003 | Hantschel et al. | |
| 6,788,086 B2 | 9/2004 | Hantschel et al. | |
| 6,880,387 B2 | 4/2005 | Kessler et al. | |
| 7,000,475 B2 | 2/2006 | Oravecz et al. | |
| 7,845,215 B2 * | 12/2010 | Cantrell et al. | 73/105 |
| 2006/0037401 A1 | 2/2006 | Shekhawat et al. | |

FOREIGN PATENT DOCUMENTS

| | | | |
|---|---|---|---|
| JP | 08-233837 | | 9/1996 |
| WO | WO 98/08046 | * | 2/1998 |

OTHER PUBLICATIONS

Shekhawat et al. *Nanoscale Imaging of Buried Structures Via Scanning Near-Field Ultrasound Holography*, Science vol. 310, 89-92 (Oct. 7, 2005).

* cited by examiner

*Primary Examiner* — Peter Macchiarolo
*Assistant Examiner* — Rose M Miller
(74) *Attorney, Agent, or Firm* — Boyle Fredrickson, S.C.

(57) ABSTRACT

A method, and corresponding apparatus, of imaging sub-surface features at a plurality of locations on a sample includes coupling an ultrasonic wave into a sample at a first lateral position. The method then measures the amplitude and phase of ultrasonic energy near the sample with a tip of an atomic force microscope. Next, the method couples an ultrasonic wave into a sample at a second lateral position and the measuring step is repeated for the second lateral position. Overall, the present system and methods achieve high resolution sub-surface mapping of a wide range of samples, including silicon wafers. It is notable that when imaging wafers, backside contamination is minimized.

34 Claims, 5 Drawing Sheets

NON-DESTRUCTIVE WAFER-SCALE SUB-SURFACE ULTRASONIC MICROSCOPY EMPLOYING NEAR FIELD AFM DETECTION

CROSS-REFERENCE TO RELATED APPLICATION

This application claims the benefit of U.S. Provisional Application No. 60/917,307, filed May 10, 2007, incorporated herein by reference in its entirety.

BACKGROUND OF THE INVENTION

1. Field of the Invention

The present application is directed to the field of metrology instruments and corresponding techniques, and more particularly to metrology tools capable of sub-surface imaging.

2. Description of Related Art

Despite broad demand from semiconductor, materials, and biomedical communities, no existing technique provides routine broadly adopted nanoscale sub-surface metrology. Surface metrology is the science of measuring small-scale features on surfaces. Surface primary form, surface waviness, and surface roughness are exemplary parameters that are measured. Sub-surface metrology is the study of parameters defining the constitution of a solid below the surface. One example of sub-surface metrology may include detecting sub-surface defects in silicon wafers. Although systems exist for sub-surface metrology, each had limitations that prevent broad application of the systems and methods, as discussed in further detail below.

Existing techniques for performing sub-surface metrology are varied, although each is associated with particular limitations. A transmission electron microscope (TEM) can see a small distance through materials of low electron density, revealing some sub-surface details. However, this technique requires destructive and time consuming thinning of samples, limiting its applicability. Scanning laser confocal microscopy can provide resolution down to roughly 200 nm, but can only be used on samples that are optically transparent. Acoustic microscopy, for example manufactured by Sonoscan, is employed very successfully for a wide range of sub-surface metrology applications. However, the lateral resolution is limited by the wavelength of the ultrasonic excitation, typically in the range of millimeters to microns. Projection x-ray systems, for example manufactured by Xradia or Skyscan, have made dramatic strides in recent years in sub-surface microscopy. However, when applied at the nanoscale, these techniques are still destructive, requiring samples that are diced to less than 25 mm across and thinned to less than 100 um in thickness. Further, the use of high energy ionizing x-ray radiation is also a consideration for many applications, where the x-rays can crosslink and/or otherwise damage samples. Pulsed thermal microscopy is another technique that provides sub-surface information by flash irradiating a sample with IR radiation and then imaging the heat re-emitting from a sample. This technique provides contrast for materials with different thermal properties, but still suffers from optical resolution limits.

Among all the techniques discussed so far, Atomic Force Microscopy (AFM) has a dramatic advantage because if can routinely produce sub-100 nm resolution, non-destructively, on a wide range of samples ranging from semiconductors, to material science, to biomedical samples. However, standard AFM imaging techniques are only sensitive to surface features or features a few nanometers below the surface. Variations of AFM that attempt to combine some of the advantages of AFM and acoustic microscopy, such as ultrasonic force microscopy and atomic force acoustic microscopy, have been evolving over the past decade. In 2005, a paper in Science described a technique called Scanning Near-field Ultrasound Holography (SNFUH). In this paper, the authors demonstrated the ability to detect and resolve 20 nm diameter nanospheres buried 500 nm below a sample surface. The paper also demonstrated the ability to observe buried voids in a semiconductor sample and malarial parasites within a red blood cell.

Despite the above listed and described systems and the potential of SNFUH, the current state of the SNFUH technique makes it completely impractical for broad adoption in industry. First, measurements have only been demonstrated on cm-scale samples, with areas more than 500× smaller than a conventional 300 mm silicon wafer. Second, to achieve sufficient contrast, the current SNFUH technique requires that an ultrasonic actuator be individually bonded to each sample. To achieve broad adoption, the semiconductor industry requires the ability to rapidly measure multiple sites (for example 15 sites) distributed across a wafer with throughput in the range of 20+/wafers per hour. There is currently no feasible technique to bond and debond ultrasonic actuators to meet these throughput requirements. As such, current SNFUH techniques are not conveniently scalable to handle large samples. Further, the semiconductor industry also places strict limits on backside particle contamination, a goal unlikely to be achieved with the current ultrasonic coupling requirements. For example, current industry standards limit the maximum number of particles added per wafer pass to less than 1000. (These standards also get tighter with each semiconductor generation.) This includes particles from all sources including wafer handling and contact between the sample holder and the wafer. Finally, the current SNFUH technique required Ph.D. level expertise with a substantial amount of experimentation to obtain a high quality image. The SNFUH introduced an ultrasonic source by driving the cantilever probe at the fixed end. The cantilever, having a length of hundreds microns, can couple Mhz ultrasonic waves to the tip effectively but will fail to couple Ghz ultrasonic wave due to attenuation of the Ghz wave along the cantilever. The architecture of the SNUHF limits its use to acoustics of Mhz frequency range What is needed is a system and method for facilitating nondestructive imaging of critical buried nanostructures with resolution exceeding 20 nm laterally and better than 1 nm vertically, including resolution of features buried more than 100 nanometers below the sample surface. What is further needed is such a system and method configured to allow such imaging over an arbitrary sample size with improved throughput. What is yet further needed is such a system and method configured to provide for minimal front and backside contamination.

SUMMARY

In accordance with an aspect of the invention, a method of non-destructively imaging sub-surface features at a plurality of locations on a sample is provided. The method includes the steps of providing a scanning probe microscope (SPM), the SPM including a probe having a cantilever bearing a tip and providing an ultrasonic source which can couple ultrasonic energy into multiple locations on a sample in rapid succession. The method includes moving at least one of the sample and the ultrasonic source with a translation to generate relative motion between the ultrasonic source and the sample, coupling an ultrasonic wave into a section of the sample at a first lateral position, and measuring the amplitude and/or phase of ultrasonic energy at or near the sample surface using the probe.

In accordance with another aspect of the invention, a probe-based instrument for detecting sub-surface features of a sample is provided. The instrument includes a scanning probe microscope (SPM), the SPM including a probe having a cantilever bearing a tip. The instrument further includes an ultrasonic source configured to provide an ultrasonic wave into a section of the sample, a translation stage configured to transport the sample relative to the probe and the ultrasonic source. The instrument yet further includes a beat signal detector, the detector measuring the amplitude and phase of ultrasonic energy near the sample with the probe, where the translation stage is configured to transport the sample relative to the probe and the ultrasonic stage to iteratively allow beat signal detection at a plurality of sections of the sample.

In accordance with yet another aspect of the invention, the above described method may further include coupling an ultrasonic wave into a second section of the sample at a second lateral position and repeating the measuring step for the second lateral position.

In accordance with yet another aspect of the invention, the above described method may further include controlling tip-sample separation using feedback loop until a non-linear response is optimized.

In accordance with another aspect of the invention, the above described method may further include providing a second ultrasonic source coupled to the probe. Providing a second ultrasonic source coupled to the probe may include integrating a piezoelectric transducer operating at GHz frequencies into the tip of the probe. This integration may be utilized to generate an ultrasonic drive wave so as to create a beat signal having a beat frequency.

In accordance with another aspect of the invention, the above described method may further include providing an ultrasonic source includes providing an ultrasonic transducer focusing generated ultrasonic waves into the section of the sample at a first lateral position. Focusing generated ultrasonic waves may include using a Fresnel lens coupled to the ultrasonic transducer to focus the waves.

In accordance with another aspect of the invention, the ultrasonic source may be driven into plural of harmonics, causing components with substantially higher frequency than the actuated frequency. High frequency components allow the diffraction limited resolution to be increased according to the harmonic frequency. Such harmonic components generally attenuate much faster than the base component, namely the first harmonics. A near field detection is desirable. Scanning probe detection in this invention should facilitate the near field detection.

In accordance with another aspect of the invention, coupling an ultrasonic wave into a section of the sample may include providing a drop of ultra pure water to couple the ultrasonic source to the sample.

In accordance with another aspect of the invention, the above described method may further include the step of reconstructing a sub-surface structure of the sample based on the measurement. In accordance with another aspect of the invention, the resolution of the reconstruction step is better than 100 nm.

These and other objects, features, and advantages of the invention will become apparent to those skilled in the art from the following detailed description and the accompanying drawings. It should be understood, however, that the detailed description and specific examples, while indicating preferred embodiments of the present invention, are given by way of illustration and not of limitation. Many changes and modifications may be made within the scope of the present invention without departing from the spirit thereof, and the invention includes all such modifications.

BRIEF DESCRIPTION OF THE DRAWINGS

Preferred exemplary embodiments of the invention are illustrated in the accompanying drawings, in which like reference numerals represent like parts throughout, and in which.

DETAILED DESCRIPTION OF THE PREFERRED EMBODIMENTS

In a preferred embodiment of the invention, a scanning probe microscope (SPM) is used to obtain information about a sample through harmonic resonance imaging (HRI). The SPM may comprise any instrument that utilizes a tip-bearing probe to obtain information concerning a sample and that is capable of oscillating the tip. It may, for instance, comprise a scanning tunneling microscope (STM), a scanning magnetic force microscope (MFM), a scanning capacitance microscope (SCM), a scanning near-field optical microscope (NSOM), a scanning thermal microscope (SThM), or an atomic force microscope (AFM). An embodiment of the invention in the form of an AFM will now be disclosed, it being understood that the invention applies to all other SPMs as well.

Figure 1:
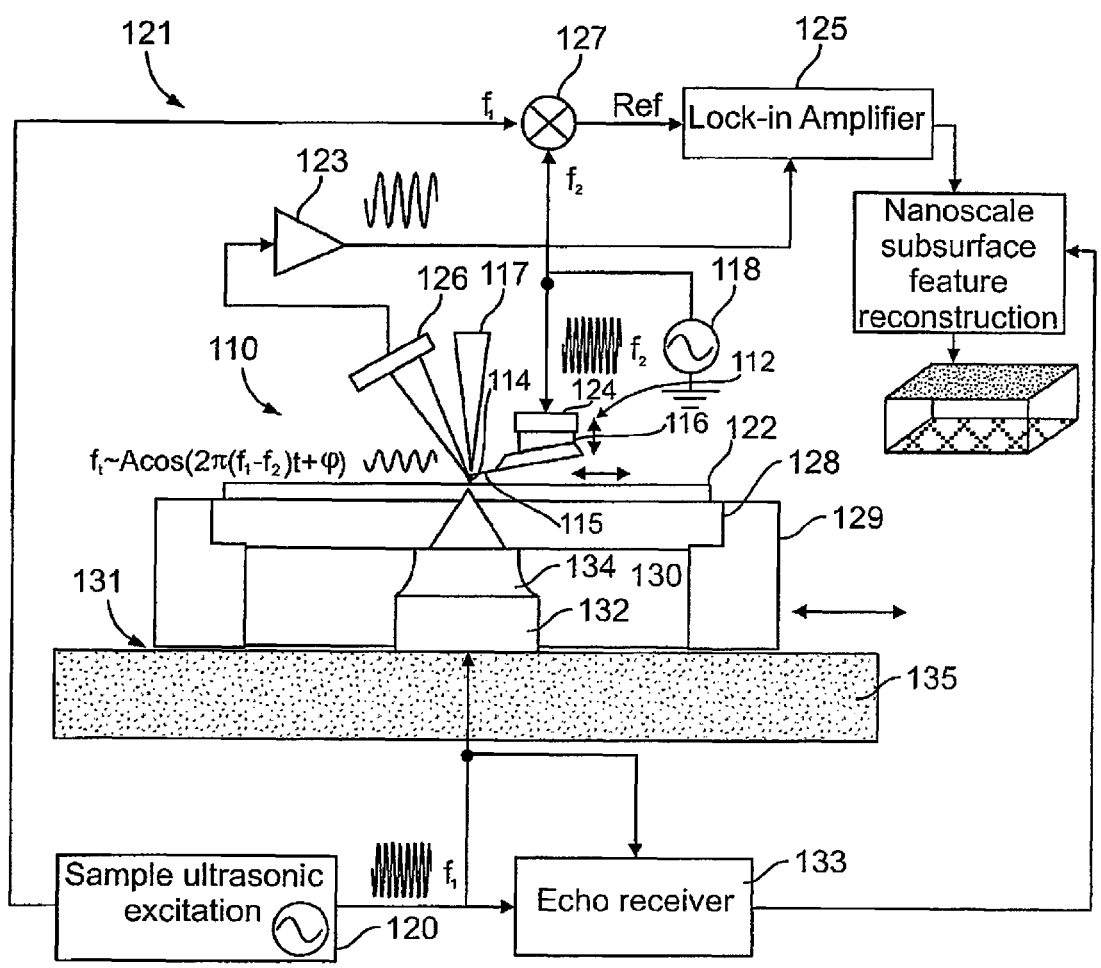
FIG. 1 is a schematic diagram of a nanoscale sub-surface metrology instrument, according to an exemplary embodiment.

Referring now to FIG. 1, a schematic diagram of a nanoscale sub-surface metrology (NSM) instrument 100 is shown, according to an exemplary embodiment. A scanning probe microscope, such as an atomic force microscope (AFM) operates by providing relative scanning movement between a measuring probe device 112 and a sample 122 while measuring one or more properties of the sample. A typical AFM system is shown schematically in FIG. 1. An AFM 110 employing a probe device 112 including a probe 114 and having a cantilever 115 is coupled to an oscillating actuator or drive 116 that is used to drive probe 114, in this case, at or near a resonant frequency of the probe (e.g., at resonance or a harmonic frequency thereof). Commonly, an electronic signal is applied from an AC signal source 118 under control of an AFM controller 121 (including, e.g., a comparator/PI gain stage 123), to cause actuator 116 to drive the probe 114 to oscillate, preferably at free oscillation amplitude $A_o$, described in further detail below with reference to FIG. 2. Probe 114 is typically actuated toward and away from sample 122 using a suitable actuator 124 or scanner controlled via feedback by controller 121. Notably, the actuator 124 may be coupled to the scanner (e.g., translation stage) 129 and probe 114 but may be, and often preferably is, formed integrally with the cantilever 115 of probe device 112 as part of a self-actuated cantilever/probe. Moreover, though the actuator 124 is shown coupled to the probe 114, the actuator 124 may alternatively be employed to move sample 122 in three orthogonal directions as an XYZ actuator, i.e., both Z motion, and X-Y scanning motion such as a raster scanning.

For use and operation, one or more probes 114 may be loaded into the AFM 110 and the AFM may be equipped to select one of several loaded probes. Selection among the differing probes may be implemented based on the required spring constant and resonance frequency range. Typically, the selected probe 114 is oscillated and brought to interact with sample 122 and sample characteristics are monitored by detecting changes in one or more characteristics of the oscillation of probe 114, as described above. In this regard, a deflection detection apparatus may be employed to direct a beam 117 towards the backside of probe 114, the beam then being reflected towards a detector 126, such as a four quadrant photodetector. As the beam translates across detector 126, appropriate signals are transmitted to controller 121, which processes the signals to determine changes in the oscillation of probe 114. Commonly, controller 121 generates control signals to maintain a constant force between the tip and sample, typically to maintain a setpoint characteristic of the oscillation of probe 114. For example, controller 121 may be used to maintain the oscillation amplitude at a setpoint value, $A_S$, to insure a generally constant average interaction between the tip and sample. Alternatively, a setpoint phase or frequency may be used. Notably, this control of tip-sample separation using a feedback loop preferably operates to maintain a nonlinear probe response to tip-sample interaction.

Figure 6:
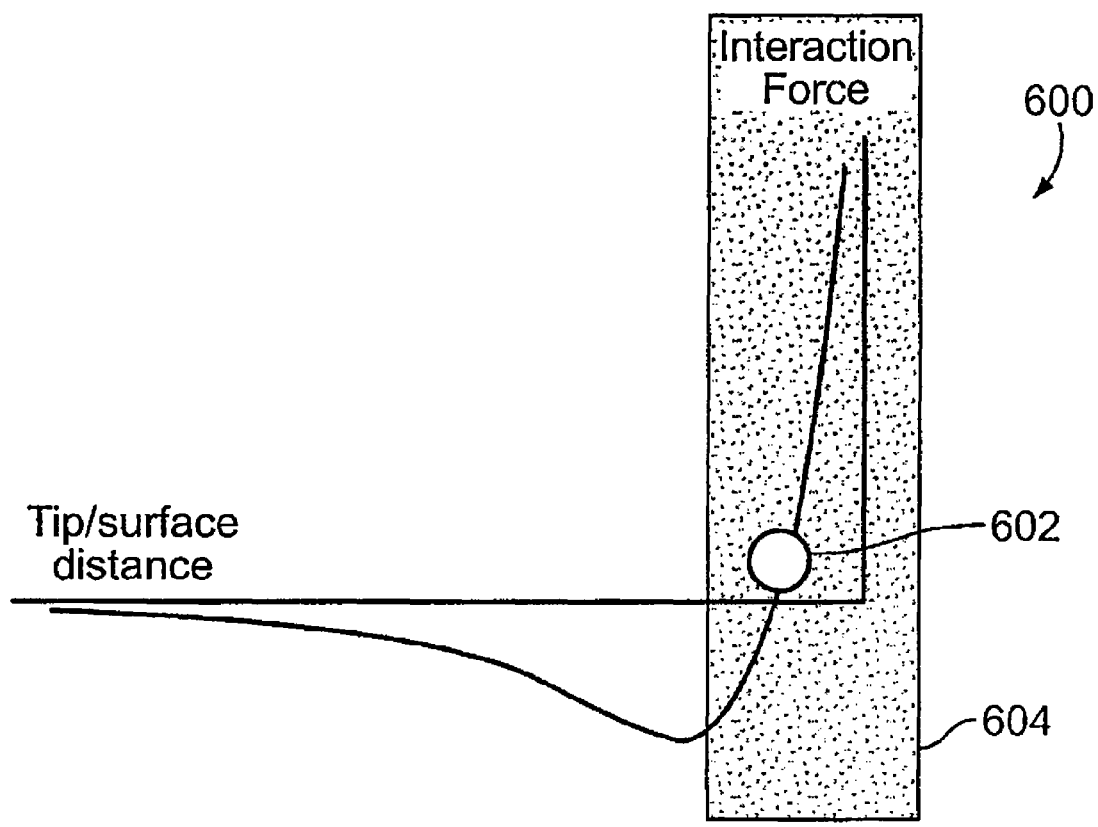
FIG. 6 is a graph illustrating tip-sample interaction as probe-sample separation is reduced, according to an exemplary embodiment.

Referring now to FIG. 6, a graph 600 illustrates the probe response to tip/sample interaction is shown, according to an exemplary embodiment. The tip approaches the sample from the left and enters a proximity contact zone 604 where interaction is initiated (before snap to contact). In this case, the force is controlled by the AFM using a feedback loop with an appropriate set point to maintain operation in the nonlinear portion of cantilever response at approximately point 602. The boundary zone, near the x axis, corresponds to the response exhibiting the highest nonlinearity. Preferably, the system optimizes response by tuning the nonlinear probe response to generate the beat signal required to use GHz frequencies in the preferred embodiments, described further herein. An exemplary desired response corresponds to a particular tip-sample separation that can be maintained by a constant average vertical deflection through the feedback loop. In an alternative operation, such separation can also be maintained by keeping a constant torsional resonance signal, which is a readily available signal at the detector 126.

Referring again to FIG. 1, a sample 122 may be an entire 300 mm silicon wafer, according to an exemplary embodiment. Sample 122 may be held on a sample holder 128 having an internal cavity 130 and an air bearing surface 131, further discussed below with reference to FIG. 3. Air bearing surface 131 may be provided to facilitate easy transportation between a translation stage 129 and a base 135 (e.g., AFM superstructure). An ultrasonic transducer 132 may be mounted inside this cavity 130. The transducer 132 may be configured to generate an ultrasonic wave in response to being driven by a source 120. Notably, the ultrasonic transducer 132 may provide continuous wave laser acoustic excitation. The ultrasonic wave is then coupled into the backside of sample 122, preferably via a liquid interface such as a drop of ultra pure water 134 between the transducer 132 and the backside of the sample 122. This permits efficient ultrasonic coupling and minimal backside contamination of the sample 122. Although a pure water coupling is described, it should be understood that the above system and method may provide alternative liquid couplings between the sample 122 and the ultrasonic source 132. In this way, the ultrasonic source may be releasably coupled to the sample 122, contrary to known systems and methods that fixedly couple the source to the sample via, for example, a permanent or semi-permanent adhesive.

The ultrasonic waves may further be focused or otherwise projected onto an area of interest of sample 122. The area of focus may further be correlated to the location of probe 114. The ultrasonic wave may be focused with an acoustic lens, such as a refractive element or a Fresnel lens. Alternatively, the ultrasonic transducer 132 may generate a plane wave that uniformly illuminates a larger area of the sample 122. A focused actuator has the advantage of more efficiently concentrating a given input energy into a smaller area. Additionally, the converging and then diverging beam reduces the energy density of background reflections. A plane wave source may have the advantage of a simpler process to invert the amplitude and phase information to obtain structure and composition information.

One advantage of the system of the present application is that the ultrasonic source(s) can be rapidly and non-destructively coupled to successive locations on a sample. By non-destructively, we mean that a sample can be imaged by this technique and still be used for its intended purpose without scrapping the part. (Many prior art techniques have required destructive sample processing and/or bonding an ultrasonic actuator with a contaminating adhesive or other material.)

As a result of the current approach, the backside contamination of the sample 122 is minimized, especially in the case that the sample 122 is a semiconductor wafer or computer hard disk head wafer. In one embodiment, the reduction in backside contamination is achieved using ultra-pure water 134 to couple the acoustic energy into the sample 122. To facilitate the coupling, plumbing and controls may be provided to the ultrasonic actuator 132 to generate and maintain drop of water 134 between the probe 114 and sample 122. Such techniques are employed, for example, in immersion lithography employed by the semiconductor industry. A water level sensor may be employed to trigger refilling of the drop 134 to compensate for evaporation. Alternatively, the humidity of the cavity 130 may be elevated to reduce evaporation to acceptable levels.

According to an alternative embodiment, cavity 130 may be filled with liquid. This arrangement further provides the benefit of effectively stiffening the sample 122 and damping any unwanted vibrations of the sample 122.

According to yet another alternative embodiment, an ultrasonic actuator 132 may be used that directly contacts the back side of the sample 122. Direct contact has the same result of effectively stiffening the area of the sample 122 being measured by the AFM 110. However, such direct contact requires a lower positioning tolerance to ensure both good mechanical coupling and low particle contamination. In one embodiment, the top surface of the ultrasonic actuator 132 may be covered with a high molecular weight polymer, for example, polyimides materials like Kapton® or Vespel®. High molecular weight polymers are both somewhat compliant and also good choices for limiting particle shedding and wafer contamination. In the case of a mechanical contact, an additional positioner, not shown, may be used to make and break contact between the bottom of the sample 122 and the ultrasonic actuator 132.

This ability to quickly reposition the ultrasonic source at different sample sections or points, using any of the above described couplings and positioning methods for the interaction between the sample, the probe device 112, and the transducer 132 provides advantages over previous systems. Further, movement of the ultrasonic source allows excitation of particular sections of the sample 122 that are currently being measured without concern regarding a distance between the section and the ultrasonic source. Accordingly, a section of the sample may be an area affected by the ultrasonic source wherein the ultrasonic energy applied to the sample 122 is relatively constant. The present system and method may be used to scan large, arbitrarily sized samples without requiring that the sample be permanently fixed in the sample holder to provide adequate ultrasonic coupling.

The arrangement shown and described herein with reference to FIG. 1 has the advantage of enabling excellent coupling from the bottom surface of the sample, while allowing high-Q resonant operation of the cantilever 115 in air above the sample 122. Alternatively, the excitation of the surface of sample 122 may be made from above using a variety of schemes. For example it is possible to build a fluid or mechanically coupled actuator surrounding the AFM cantilever 115 and probe 114. Alternatively, laser pulses can be used to generate thermoacoustic waves that can be imaged in the near field by the AFM probe 114. It is also possible to use air-coupled actuators and/or electromagnetic acoustic transducers (EMATs) above or below the sample.

Figure 2:
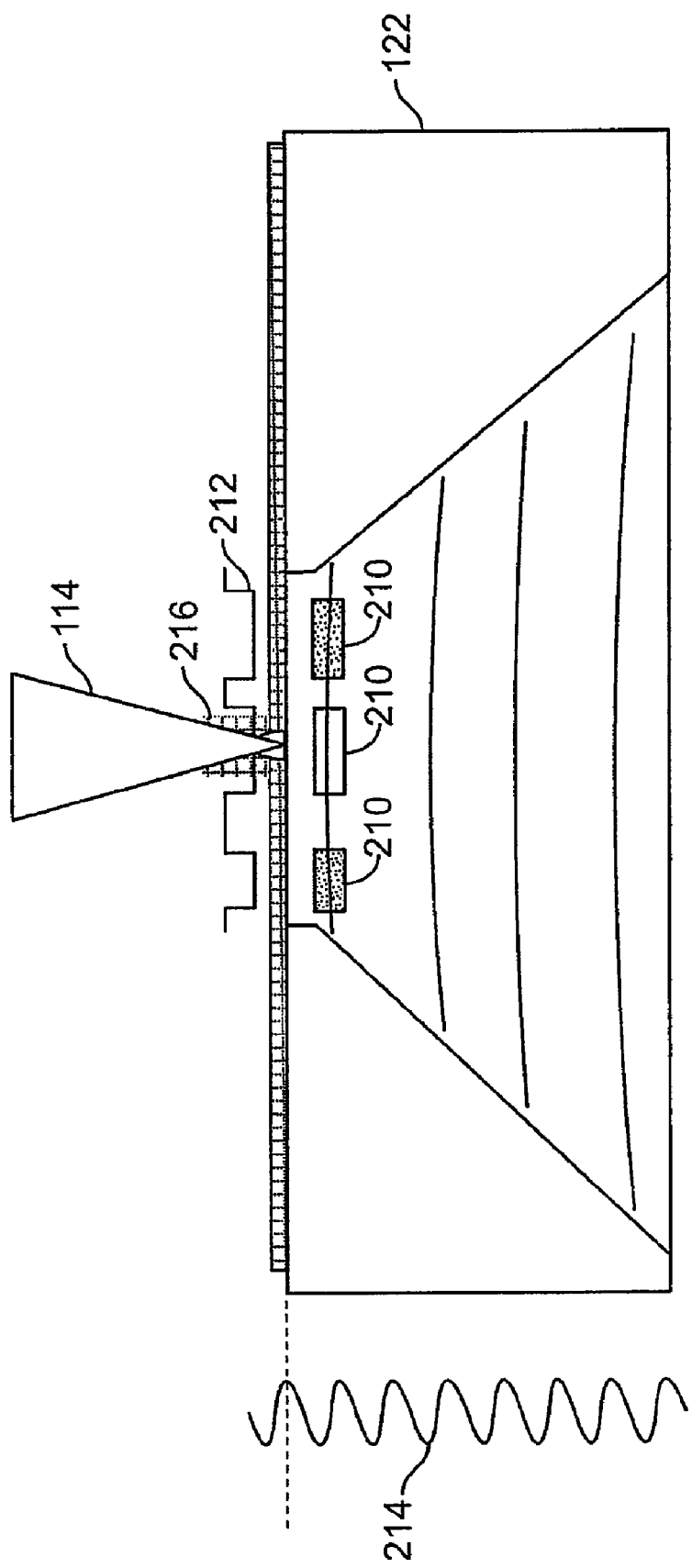
FIG. 2 is a schematic illustration of the interaction of an ultrasonic wave produced by a transducer of the invention and sub-surface sample features, according to an exemplary embodiment.

Referring now to FIG. 2, a schematic illustration of the interaction of an ultrasonic wave produced by a transducer of the invention and sub-surface sample features is shown, according to an exemplary embodiment. Sub-surface features 210 inside the sample 122 interact with the ultrasonic waves according to the acoustic impedance of the different features 210. These interactions produce signal attenuation and/or phase delays in the propagation of ultrasonic wavefronts 214. These wavefront distortions may then detected in the near field using the probe 114 of an AFM cantilever 115.

The AFM probe 114 monitors the ultrasonic energy 214 that propagates to the surface of sample 122. Notably, interaction between ultrasonic energy (e.g., incident ultrasonic wave) and sub-surface features can result in attenuation, reflection, retardation, refraction and/or diffraction of the ultrasonic energy. If the sample 122 is being observed in ambient environment, the air-sample interface at the sample's top surface may reflect the vast majority of the incident ultrasonic energy. In some cases, a surface acoustic wave 212 may be generated at the surface of sample 122 that can be directly detected by the AFM. In addition, a small decaying field 216, called the "evanescent field" extends above the sample surface. When the AFM tip of probe 114 is placed in this evanescent field 216, the ultrasonic energy 214 can couple to the tip of probe 114 generating measurable motion of the cantilever 115. The presence of a fluid meniscus layer that forms between the tip and sample surface likely enhances the degree of this coupling.

Measuring the evanescent field with the AFM tip of probe 114 overcomes far field diffraction resolution limit and allows mapping of ultrasonic wavefronts with nm-scale resolution. The ultrasonic excitation frequency $f_1$ of source 120 used to drive transducer 132 may be in the range of 2-200 MHz, and more preferably larger, depending on penetration depth and resolution required. Since the frequency $f_1$ is often above the typical detection bandwidth of conventional AFMs, a "down conversion" scheme may be employed to enable detection of the ultrasonic wavefront.

Down conversion is implemented by converting a signal at a high frequency to a lower frequency that is more easily measured by the system 100. Down conversion is achieved in system 100 by applying an additional ultrasonic oscillating signal at frequency $f_2$ to, for example, the base of the AFM cantilever 115, or more preferably nearer the tip when using a self-actuated probe. In the case that there is a nonlinear interaction between the AFM tip of probe 114 and the sample 122, this interaction generates a force on the tip of probe 114 that is proportional to the difference between $f_1$ and $f_2$. Specifically, there is a time varying force component on the tip of probe 114 equal to $F_t$:

$$F_t = \gamma A_c A_s \cos(2\pi(f_1-f_2)t+\phi);$$

where $\gamma$ is the strength of the nonlinear interaction, $A_s$ is the amplitude of the sample surface motion at frequency $f_1$, $A_c$ is the amplitude of the cantilever motion at $f_2$, and $\phi$ is the accumulated phase delay during the propagation of the wavefront.

Super-wavelength resolution is achieved using one or more of the following techniques. It has been shown that the ability to achieve resolution in excess of the diffraction limit by employing high energy ultrasonic excitation that elicits nonlinear material responses. The nonlinear response creates a harmonic distortion to elastic waves propagating through the material. This harmonic distortion is equivalent to the generation and propagation of higher harmonics of the original excitation. Since the higher harmonics have shorter wavelengths the diffraction limited resolution can be higher than the fundamental excitation.

More specifically, if a high intensity ultrasonic wave is launched into the sample at frequency $f_1$, the harmonic distortion will create harmonics at frequencies $nf_2$, when n is an integer multiple. With the AFM cantilever detection, it is possible to arrange for amplified detection of a selected harmonic by arranging $nf_2-f_1 \approx f_0$, where $f_0$ is the cantilever resonant frequency. For example, if $f_2$ is 200 MHz, and $f_1$ is 1001 MHz, the $5^{th}$ harmonic of $f_2$ will generate a beat frequency of $nf_2-f_1=1$ MHz. If the AFM cantilever is arranged to have a resonant frequency of 1 MHz and a Q of 1000, for example, this will enhance the detection sensitivity of the ultrasound harmonic by 1000×, while simultaneously increasing the 3D spatial resolution of the excitation wave. When this is combined with near field detection by the nm scale AFM tip interaction it provides unprecedented 3D sub-surface resolution. Notably, though the beat signal is preferably tuned to a resonance of the probe (fundamental or harmonic), the frequency can be anywhere in the detectable region of the resonance, i.e., it need not be at the peak.

Referring again to FIG. 1, a lock-in amplifier 125 may be used to extract the amplitude and phase of these time varying forces. The lock-in amplifier 125 can be implemented in analog electronics, through digital computation, or a combination of both. A frequency mixer 127 generates a signal at the frequency $f_1-f_2$ that is then sent to the lock-in amplifier 125 as a reference signal. The lateral extent of the nonlinear interaction $\gamma$ may be confined to a very small area roughly corresponding to the contact or near-contact radius of interaction between the tip of probe 114 and sample 122. According to one exemplary embodiment, a 1 GHz wave may be launched from the sample 122 with a displacement field of 0.01 nm under the probe 114. Another wave may be excited by the GHz actuator on the AFM probe 114 apex with the frequency of 1.001 GHz. This second wave may be referred to as an ultrasonic drive wave and be configured to create a beat signal having a beat frequency. The difference of these two frequencies may be chosen to be the contact resonance frequency of 1 MHz with a cantilever spring constant of 40 N/m and tip radius 10 nm. For this reason, ultrasonic forces that act on the apex of the tip 114 contribute substantially to the measured signals and may be quantified.

The tip 114 may be scanned relative to the sample 122 and the amplitude and phase information may be recorded as a function of lateral position. This scanning mechanism is not shown in FIG. 1 for clarity, but may be implemented using one or more piezoelectric scanning devices that scans the sample 122, the tip 114, or a combination thereof. The scanner may also employ an alternative fine translation mechanism, such as magnetostrictive, electrostrictive, capacitive, inductive, thermal, or other motion inducing mechanisms.

Figure 3:
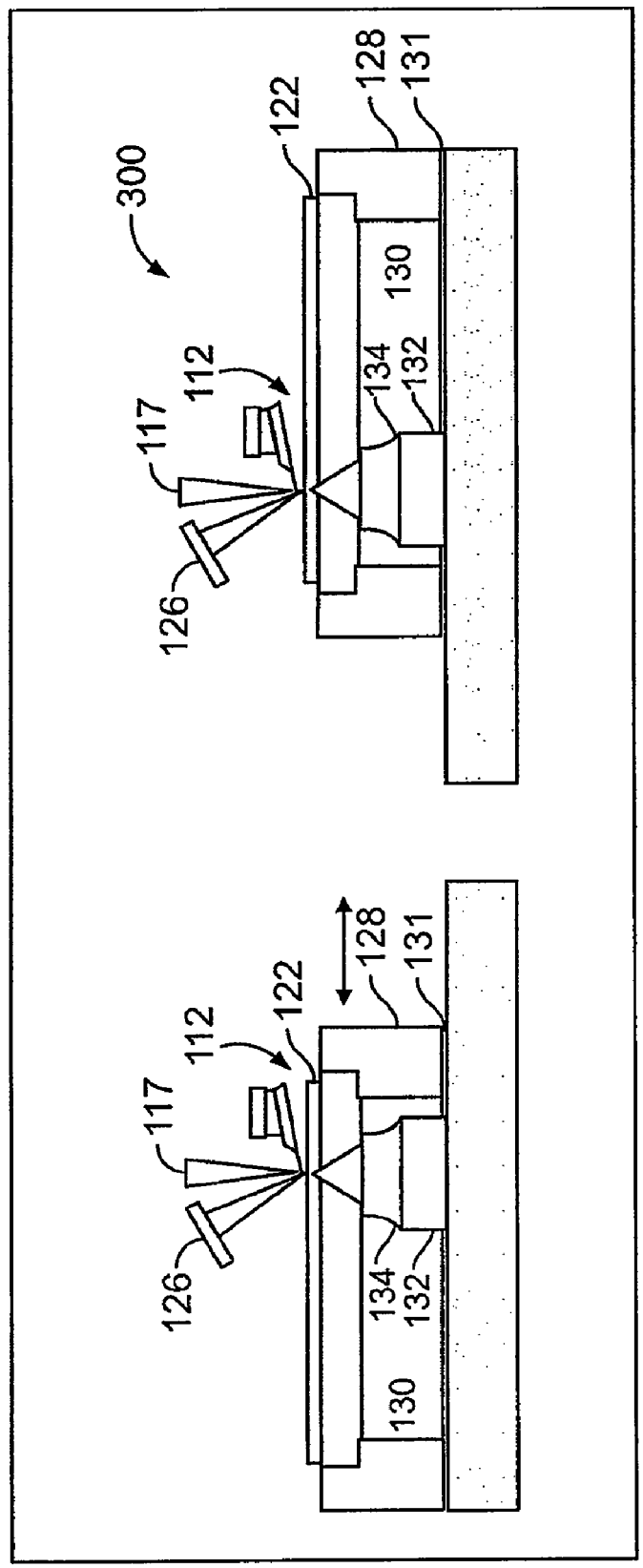
FIG. 3 is a side elevation of a sample holder, illustrating sub-surface feature measurement over widely separated areas on a large sample, according to an exemplary embodiment.

Referring now to FIG. 3, a side elevation 300 of a sample holder 128, illustrating the sequential observation of widely separated areas on a large sample 122, is shown, according to an exemplary embodiment. The side elevation 300 shows the process of observing widely separated areas on a large sample 122. As mentioned above with reference to FIG. 1, the sample holder 128 contains an internal cavity 130 to allow the placement of the ultrasonic actuator 132 under the sample 122. The sample holder 128 may be translated laterally so that the AFM probe 114 and the acoustic actuator 132 are aimed at different areas of the sample 122. Two such example positions are shown in FIG. 3 below, but this technique allows an arbitrary array of sample areas to be observed. In fact, the ultrasonic actuator 132 below the sample and the optical detection laser 117 and detector 126 can be used to quickly scan large areas of the sample 122 using traditional acoustic microscopy techniques. This scanning method can provide coarse preview scans to allow the AFM 110 to focus on areas of particular interest, for example a suspect region identified in the acoustic survey scan.

According to an exemplary embodiment, the sample holder 128 may be translated using a translation stage 129. One suitable translation stage is a high speed air bearing stage. Other examples include crossed roller-bearing stages, ball bearing stages, drag stages, flexure stages or other mechanical translation devices with a range of motion matching the area of the samples desired to be accessible. Alternately, the translation stage could be a gimbaled or tilt stage that changes the angle of the ultrasonic source and the direction of its output. These stages can be driven with stepper motors, servo motors, linear motors, piezoelectric devices or other devices capable of moving the stage over the desired range.

For simplicity in the drawings, the bottom of the sample holder 128 is shown as the air bearing surface 131. While this is a feasible implementation, in practice the sample holder 128 and the translation stage may be separate units. The translation stage typically allows translation in at least two lateral axes (e.g., XY plane) and can include an additional vertical translation stage to adjust the height of the sample 122.

The amplitude and phase data as a function of lateral position over the sample may then used to reconstruct sub-surface structure for sample 122. This inversion process calculates the most likely structure and composition that would match the measured distribution of amplitude and phase. When possible, information about the sample's expected composition and structure may be used to make the inversion of amplitude and phase data faster and more accurate. The resulting data may be stored and displayed, for example showing the structural and or compositional details in each vertical layer of the sample 122. Additional information about the composition and structure of sample 122 may be obtained by measuring the dispersion of amplitude and phase delays as a function of different frequencies $f_1$ and $f_2$. These multi-spectral measurements can be made by sweeping or chirping the excitation frequencies over a desired range.

In cases of ambiguity about the depth of a sub-surface feature 210, one of several techniques can be employed, particularly when the ultrasonic source 132 is coupled to the sample from the top surface, the same side of the secondary ultrasonic source coupled through the tip. First, the use of a focused ultrasonic actuator can limit the depth of focus and hence the region of a sample that is excited. Second, pulse-echo/time of flight measurements from the ultrasonic transducer can be used to locate the vertical position of interface layers. Existing acoustic microscopy techniques, for example, allow the localization of buried interface layers with nm or sub-nm scale precision. For this purpose, a pulse generator may be connected to the ultrasonic actuator and the resulting echo detected by an echo receiver 133. The time delay between the pulse and echo indicate the distance traveled by the ultrasonic wave, thus localizing the vertical position of a sub-surface interface. Additionally, it is possible to use the cantilever tip to detect the transmission time of the pulses through the body of the sample. Such time of the flight exhibits itself as the phase delay in the beat signal, yielding the depth information through the phase changes.

For additional assistance in reconstructing the sub-surface structure accurately, it is possible to use tomographic techniques, for example by adjusting the angle of the incident ultrasonic wave. This can be done by rotating the ultrasonic source, or for example, by using a phased array of actuators to guide the direction of the outgoing ultrasonic wave. By assembling multiple 2D projections of amplitude and phase at multiple incidence angles it is possible to accurately reconstruct the details of sub-surface structure.

Figure 4:
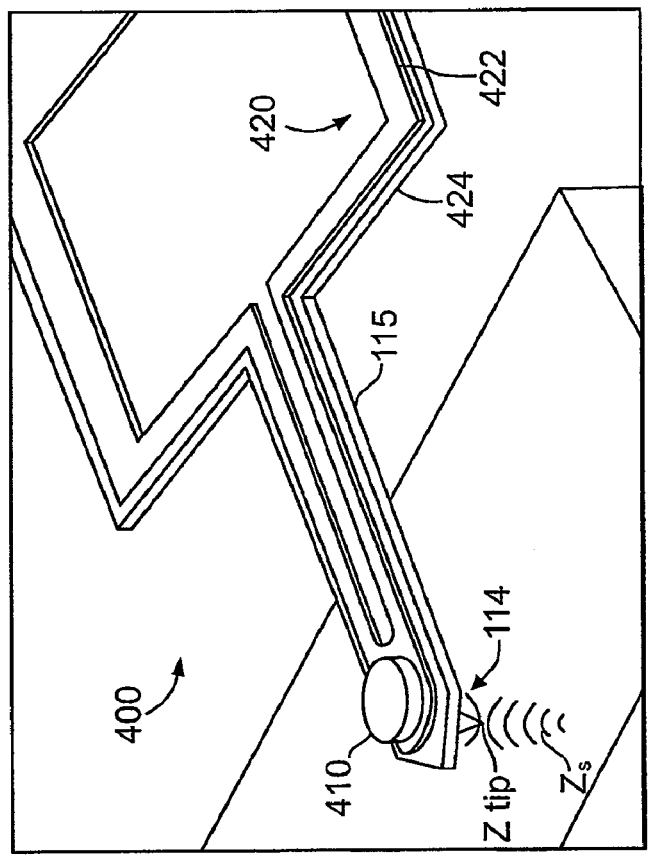
FIG. 4 is a system for achieving the nonlinear tip-sample mixing by creating a local GHz level excitation right above an AFM probe, according to an exemplary embodiment.

Referring now to FIG. 4, a system 400 for achieving the nonlinear tip-sample mixing by creating a local GHz level excitation right above the AFM probe 114 is shown, according to an exemplary embodiment. AFM probes 114 with integrated zinc oxide tips (ZnO) may be couple to a high frequency ultrasonic source. Drive voltages will be delivered to a GHz tip actuator 410 by way of a coplanar waveguide 420. Coplanar waveguide 320 may be configured to include a base 424 having an electrode 422. A zinc oxide thickness of about 2.9 µm may be provided to achieve a 1 GHz frequency. The shape of the actuator 420 plate pattern determines the occurrence of the power maximum at the tip apex. Modeling of the acoustic emission and the process design of the tip geometry will help to optimize the ultrasonic output power at the apex. The mixing of the two waves $Z_{tip}$ and $Z_s$, as shown in FIG. 4, will result in a beat force $F_t$ at the cantilever resonance frequency. The magnitude of the beat force is a function of the tip-sample interaction controlled by the AFM.

Figure 5:
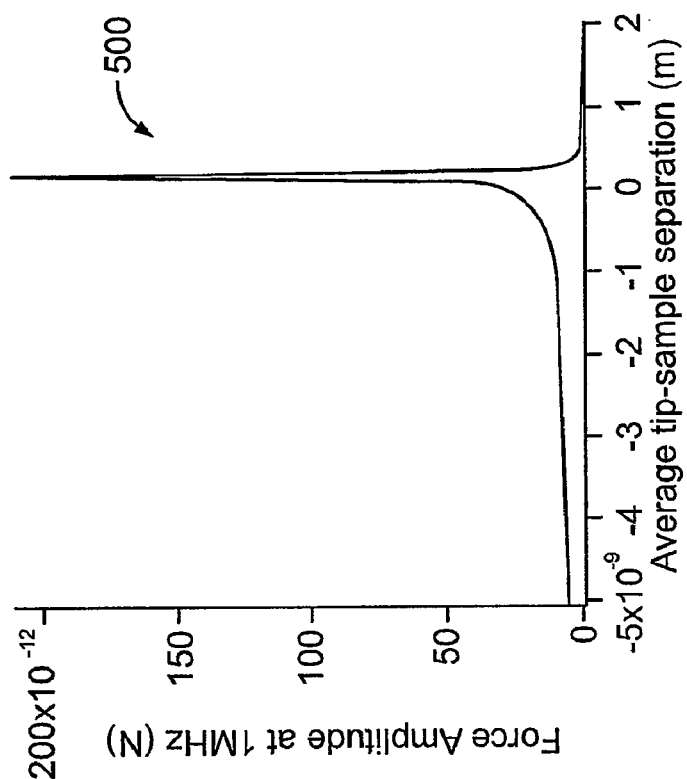
FIG. 5 is a graph displaying the variation of the beat force as the tip interacts with the sample from non-contact (positive separation) to repulsive contact (negative separation), according to an exemplary embodiment.

Referring now to FIG. 5, a graph 500 displaying the variation of the beat force as the tip interacts with the sample from non-contact (positive separation) to repulsive contact (negative separation) is shown, according to an exemplary embodiment. As shown in graph 500, only very modest intensity of the tip wave $Z_{tip}$ is required. The response curve 500 illustrates that a maximum beat force was determined near the zero separation. This maximum corresponds to a desired operating condition for the beat signal detection. AFM can maintain such separation either by maintaining a constant vertical deflection (contact mode) or constant torsional resonance amplitude (TRmode™) with a feedback loop.

Notably, including the ultrasonic drive at or near the base of the probe or cantilever has the disadvantage of not efficiently coupling the ultrasonic energy to the probe tip given that the lever is soft, i.e., it operates as a low pass filter in this regard. Driving the probe with this second source 410 of ultrasonic energy using a self-actuated probe including an integrated piezoelectric element (e.g., ZnO), on the other hand, operates to more efficiently couple the ultrasonic energy to the tip. This facilitates generation of the beat signal.

Advantageously, the above described system and method provides for numerous advantages over existing systems. Using a laser acoustic source collocated with AFM tip 114, the system allows for arbitrary positioning of ultrasonic excitation. Further, using a high harmonic ultrasound source 132 and near field AFM detection, the above described system and method allows for higher subsurface lateral resolution which is at least 2 times better than the diffraction limit.

Although the best mode contemplated by the inventors of carrying out the present invention is disclosed above, practice of the present invention is not limited thereto. It will be manifest that various additions, modifications and rearrangements of the features of the present invention may be made without deviating from the spirit and scope of the underlying inventive concept. The scope of still other changes to the described embodiments that fall within the present invention but that are not specifically discussed above will become apparent from the appended claims and other attachments.

The invention claimed is:

1. A method of imaging sub-surface features of a sample, the method comprising the steps of:
providing a scanning probe microscope (SPM), the SPM including a probe having a cantilever bearing a tip;
providing an ultrasonic source that directs ultrasonic energy into the sample;
coupling the ultrasonic energy from the ultrasonic source into a section of the sample at a first position;
using the probe to detect an interaction between the incident ultrasonic energy and a sub-surface feature of the sample;
successively moving at least one of the sample and the ultrasonic source with a translation stage to generate relative motion between the ultrasonic source and the sample so as to couple ultrasonic energy into different sections of the sample; and
further including providing a second ultrasonic source coupled to the probe that produces an ultrasonic drive wave so as to create a beat signal having a beat frequency, thereby down converting the detected interaction.

2. The method of claim 1, further including coupling an ultrasonic wave into the sample at a second position and repeating the measuring step for the second position.

3. The method of claim 2, wherein coupling an ultrasonic wave into the sample is nondestructive to the sample.

4. The method of claim 1, further including controlling tip-sample interaction so as to elicit a nonlinear probe response.

5. The method of claim 4, wherein controlling tip-sample interaction includes tuning the non-linear probe response using feedback.

6. The method of claim 1, wherein providing a second ultrasonic source coupled to the probe includes integrating a piezoelectric transducer operating at GHz frequencies with the probe.

7. The method of claim 1, wherein providing an ultrasonic source includes providing a ultrasonic transducer focusing generated ultrasonic waves into the section of the sample at the first position.

8. The method of claim 7, wherein focusing generated ultrasonic waves includes using a Fresnel lens coupled to the ultrasonic transducer to focus the waves.

9. The method of claim 7, wherein the ultrasonic source is driven to excite plural harmonics.

10. The method of claim 1, wherein coupling an ultrasonic wave into a section of the sample includes providing a liquid coupling of the ultrasonic source to the sample.

11. The method of claim 1, wherein coupling an ultrasonic wave into a section of the sample includes continuous wave laser acoustic excitation.

12. The method of claim 1, further comprising the step of reconstructing a sub-surface structure of the sample based on the detected interaction, and wherein the resolution of the reconstruction step is better than 100 nm.

13. The method of claim 1, wherein said using step includes measuring at least one of amplitude and phase of cantilever motion.

14. The method of claim 1, wherein measuring the amplitude and phase of ultrasonic energy includes using at least one of a group including an expected composition and an expected structure for the sample to guide the measurement.

15. The instrument of claim 1, wherein the moving step provides translation between at least first and second sections of the sample in less than 5 minutes.

16. The instrument of claim 1, wherein the moving step provides translation between at least first and second sections of the sample in less than 10 seconds.

17. The method of claim 1, wherein the beat frequency is tuned to a frequency corresponding to a resonant frequency of the probe.

18. The method of claim 17, wherein the ultrasonic energy has a corresponding frequency, $f_1$, and the ultrasonic drive wave has a frequency, $f_2$, and wherein the relationship $nf_2 - f_1$ is substantially equal to a resonant frequency of the probe, wherein n is an integer multiple corresponding to a harmonic of $f_2$.

19. A probe-based instrument for detecting sub-surface features of a sample, the instrument comprising:
a scanning probe microscope (SPM), the SPM including a probe having a cantilever bearing a tip;
an ultrasonic source configured to provide an ultrasonic wave into a section of the sample at a first position;
a translation stage that provides relative movement between the sample relative to both the probe and the ultrasonic source;
a beat signal detector, the detector measuring an interaction between the incident ultrasonic energy and a sub-surface feature of the sample;
a second ultrasonic source coupled to the probe that produces an ultrasonic drive wave so as to create a beat signal having a beat frequency, and thereby down converting the detected interaction.

20. The probe-based instrument of claim 19, further including an actuator controlling tip-sample separation using a feedback loop until a non-linear response of the probe is optimized.

21. The probe-based instrument of claim 19, wherein the sample is a semiconductor wafer of at least 200 mm in diameter.

22. The probe-based instrument of claim 19, wherein the ultrasonic coupling is non-destructive to the sample.

23. The probe-based instrument of claim 22, wherein fewer than 1000 particles are added to the backside of the wafer by the coupling and measurement steps.

24. The probe-based instrument of claim 19, wherein the ultrasonic source is coupled to the sample via a liquid.

25. The probe-based instrument of claim 19, wherein the interaction causes cantilever motion, and wherein the detector measures at least one of amplitude and phase of the cantilever motion.

26. The instrument of claim 19, wherein the ultrasonic wave has a corresponding frequency, $f_1$, and the ultrasonic drive wave has a frequency, $f_2$, and wherein the relationship $nf_2-f_1$ is substantially equal to a resonant frequency of the probe, wherein n is an integer multiple corresponding to a harmonic of $f_2$.

27. A method of imaging sub-surface features locations of a sample, the method comprising the steps of:
providing a probe having a cantilever and a probe tip;
providing first and second ultrasonic sources generating first and second ultrasonic waves that are successively coupled into different locations on the sample;
providing at least one translation stage configured to provide relative motion between the sample and the first and second ultrasonic sources;
coupling an ultrasonic wave from the first ultrasonic source into a section of the sample;
driving the probe with ultrasonic energy from the second ultrasonic source;
measuring ultrasonic energy substantially at the sample surface caused by an interaction of the ultrasonic energy from the first and second ultrasonic sources;
moving at least one of the sample, the first ultrasonic source, and the second ultrasonic source to generate relative motion and to allow measurement at a second section of the sample; and
wherein the measurement of the ultrasonic energy includes detection of a beat signal generated by coupling of at least one of the harmonics of the first ultrasonic source and the second ultrasonic source, the beat signal representing a down conversion of the detected interaction.

28. The method of claim 27, wherein providing a second ultrasonic source coupled to the probe includes integrating a piezoelectric transducer operating at GHz frequencies into the tip of the probe.

29. The method of claim 28, wherein the tuning step includes a feedback loop.

30. The method of claim 27, further including tuning a non-linear response of the probe to probe sample interaction so as to create a beat signal having a frequency substantially corresponding to one of the probe resonances.

31. The method of claim 27, wherein coupling the ultrasonic wave from the first ultrasonic source into a section of the sample includes providing a liquid coupling of the ultrasonic source to the sample.

32. The method of claim 27, further comprising the step of reconstructing a sub-surface structure of the sample based on the measurement and wherein the resolution of the reconstruction step is better than 100 nm.

33. A method of imaging sub-surface features at a plurality of locations on a sample, the method comprising the steps of:
releasably coupling an ultrasonic wave to a sample;
exciting a probe of a scanning probe microscope with an ultrasonic signal having a frequency greater than 1 GHz;
positioning the probe relative to the sample to optimize a non-linear reaction between the probe and the sample; and
detecting a beat signal to detect subsurface features of the sample to a resolution greater than 20 nm.

34. The method of claim 33, wherein the releasably coupling step includes providing a source that generates the ultrasonic wave in an internal cavity of a sample holder, and wherein the ultrasonic wave is coupled to the sample via a liquid interface.

* * * * *